(12) United States Patent
Moreno et al.

(10) Patent No.: US 8,173,420 B2
(45) Date of Patent: May 8, 2012

(54) CELL SEEDING MODULE

(75) Inventors: Maria J. Moreno, Ottawa (CA); Philippe Levesque, Bloomington, MN (US); Jacob M. Thibodeau, Minneapolis, MN (US)

(73) Assignee: Tissue Growth Technologies Corporation, Minnetonka, MN (US)

( * ) Notice: Subject to any disclaimer, the term of this patent is extended or adjusted under 35 U.S.C. 154(b) by 465 days.

(21) Appl. No.: 12/402,427

(22) Filed: Mar. 11, 2009

(65) Prior Publication Data

US 2010/0233811 A1 Sep. 16, 2010

(51) Int. Cl.
*C12M 1/00* (2006.01)

(52) U.S. Cl. .................... 435/289.1; 435/309.1

(58) Field of Classification Search .......... None
See application file for complete search history.

(56) References Cited

U.S. PATENT DOCUMENTS

| | | |
|---|---|---|
| 3,651,607 A | 3/1972 | Lee, II |
| 4,130,120 A | 12/1978 | Kohler, Jr. |
| 5,441,539 A | 8/1995 | Alchas et al. |
| 5,460,968 A | 10/1995 | Yoshida et al. |
| 5,492,826 A | 2/1996 | Townsend et al. |
| 5,670,708 A | 9/1997 | Vilendrer |
| 6,080,581 A | 6/2000 | Anderson et al. |
| 6,121,042 A | 9/2000 | Peterson et al. |
| 6,238,908 B1 | 5/2001 | Armstrong et al. |
| 6,794,184 B1 | 9/2004 | Mohr et al. |
| 6,979,308 B1 | 12/2005 | MacDonald et al. |
| 7,051,654 B2 | 5/2006 | Boland et al. |
| 7,179,287 B2 | 2/2007 | Wolfinbarger, Jr. |
| 7,229,820 B2 | 6/2007 | Wilson |
| 7,270,472 B2 | 9/2007 | Carreras |
| 7,348,175 B2 | 3/2008 | Vilendrer et al. |
| 7,410,792 B2 | 8/2008 | Vilendrer |
| 7,439,057 B2 | 10/2008 | Frangos et al. |
| 7,456,019 B2 | 11/2008 | Goodwin et al. |
| 7,472,604 B2 | 1/2009 | Moore, Jr. et al. |
| 7,587,949 B2 | 9/2009 | Dingmann et al. |
| 7,624,648 B2 | 12/2009 | Nickel et al. |
| 7,694,593 B2 | 4/2010 | Owens et al. |
| 2005/0101008 A1 | 5/2005 | Diresta et al. |
| 2008/0187599 A1 | 8/2008 | Dimuzio et al. |
| 2009/0018386 A1 | 1/2009 | Wolf et al. |

FOREIGN PATENT DOCUMENTS

WO 2007/147232 A1 12/2007

*Primary Examiner* — Jim Ketter

(74) *Attorney, Agent, or Firm* — Dietz Law Office LLC

(57) ABSTRACT

An apparatus and method is described for seeding cells on a sample or specimen. The cells may be selectively and locally seeded on an upper and lower surface of a planar sample or specimen or on either or both of an interior luminal surface and exterior surface of a hollow sample or specimen. The apparatus includes a chamber suitable for cell seeding, cell growth, and cell conditioning.

19 Claims, 9 Drawing Sheets

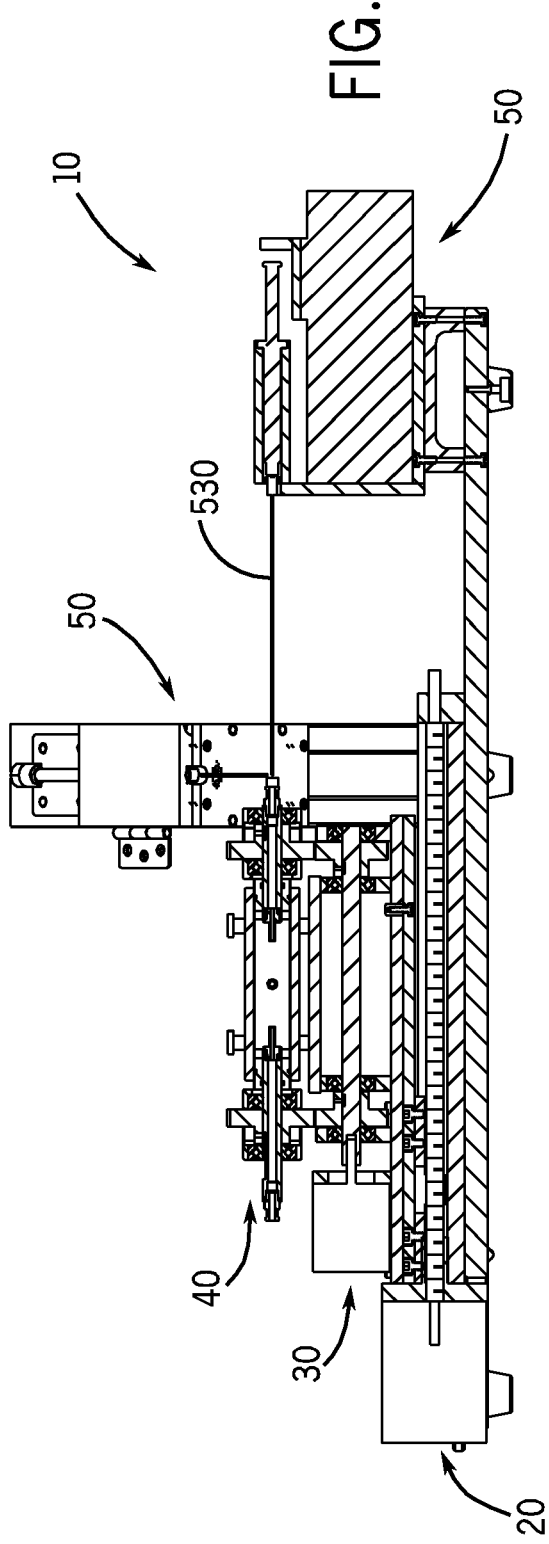
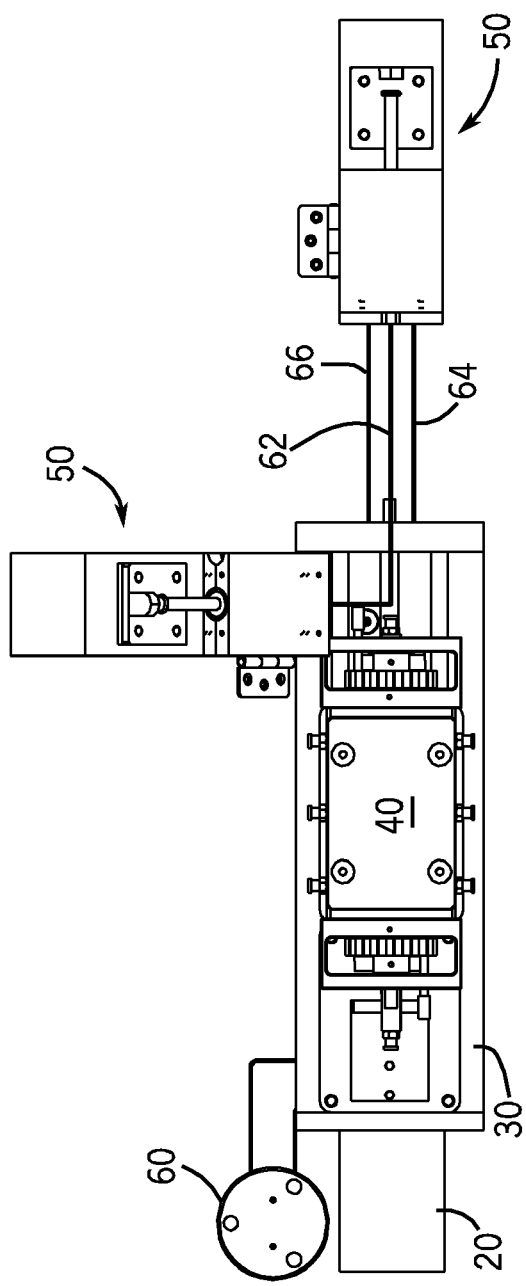

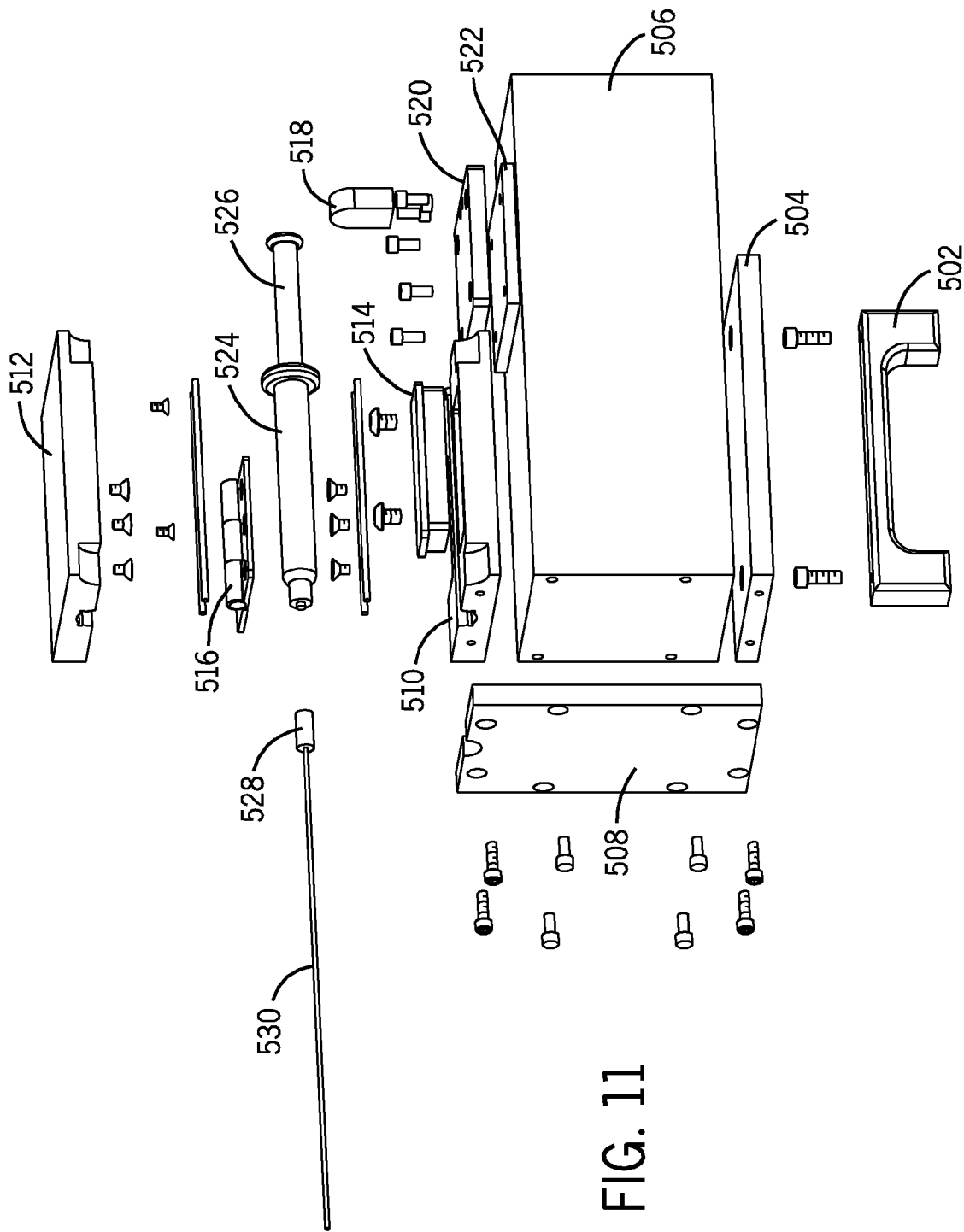

CELL SEEDING MODULE

CROSS-REFERENCE TO RELATED APPLICATIONS

Not Applicable

FEDERAL SPONSORSHIP

Not Applicable

JOINT RESEARCH AGREEMENT

Not Applicable

TECHNICAL FIELD

This invention pertains generally to a method and apparatus to deposit cells within a chamber. This invention also pertains to a portable chamber for cell growth capable of maintaining a sterile system closed to an external environment.

BACKGROUND

Generally, growth of cells on tissue, vascular grafts, biomedical prosthesis, substrate, and other medical devices (hereinafter referred to simply as a sample or specimen) has previously been described. Prior devices capable of depositing and growing cells typically submerge the sample with a cell suspended media, attempting to deposit cells uniformly on the entire sample. Often, pressure or other forces are used to influence adhesion of the cells on the sample. Many of these devices are designed for depositing cells onto a particularly shaped sample. By way of example, prior devices describe seeding cells on one surface of a biological vascular graft.

Other prior devices describe techniques for depositing a complex arrangement of an array of cells onto relatively planar substrates. For example, a multi step approach to deposit cells has been utilized to thereby build layers of proteins and cells utilizing masks to control the location of deposition and exposure of the cells on an exterior surface of the substrate. Other printing methods have been contemplated to, in essence, print cells onto an exterior surface of a Petri dish, glass, paper, plastic or other relatively planar substrate.

SUMMARY

Embodiments of the invention include an apparatus and method for a localized deposition of cells in a predefined pattern onto either a planar or three dimensional specimen or sample, including a tissue construct, vascular graft, biomedical prosthesis, or other medical device. The sample may be rotated while the cells are deposited onto the sample. Alternatively, the sample may be actuated linearly to deposit a row of cells in a straight line on the sample. In an embodiment of the invention, a tubular specimen or sample having a lumen may have cells deposited on one or both of an inner luminal surface and an exterior surface of the sample. Further, the tubular sample may be rotated or linearly actuated to thereby deposit cells locally on the sample to create a ring or linear pattern on either or both of the interior and exterior of the tubular sample. Alternatively, the sample may be both rotated and linearly actuated while depositing localized cells on the sample to create multiple variations of curvilinear patterns on the three dimensional sample.

Also described herein is an interchangeable, portable, chamber system that is capable of holding and rotating the sample within the chamber. The cells may be deposited on the sample contained within a sealed or pressurized chamber. The chamber provides for multiple ports to facilitate the delivery of nutrients, fluids, or gases within the chamber. Further, the chamber is suitable for use with other instrumented and servo controlled devices to allow for conditioning the sample and is particularly well suited for use with the bioreactors described in U.S. Pat. No. 7,410,792 and U.S. Pat. No. 7,348,175.

The accompanying drawings, which are incorporated in and constitute a portion of this specification, illustrate embodiments of the invention and, together with the detailed description, serve to further explain the invention. The embodiments illustrated herein are presently preferred; however, it should be understood, that the invention is not limited to the precise arrangements and instrumentalities shown. For a fuller understanding of the nature and advantages of the invention, reference should be made to the detailed description in conjunction with the accompanying drawings.

DESCRIPTION OF THE DRAWINGS

In the various figures, which are not necessarily drawn to scale, like numerals throughout the figures identify substantially similar components.

FIG. 2 is a partial sectional view of the cell seeding module of the type shown in FIG. 1;

FIG. 3 is a top plan view of the cell seeding module of the type shown in FIG. 1;

FIG. 11 is an exploded perspective view of a delivery system of the type shown in FIG. 10.

DETAILED DESCRIPTION

Figure 1:
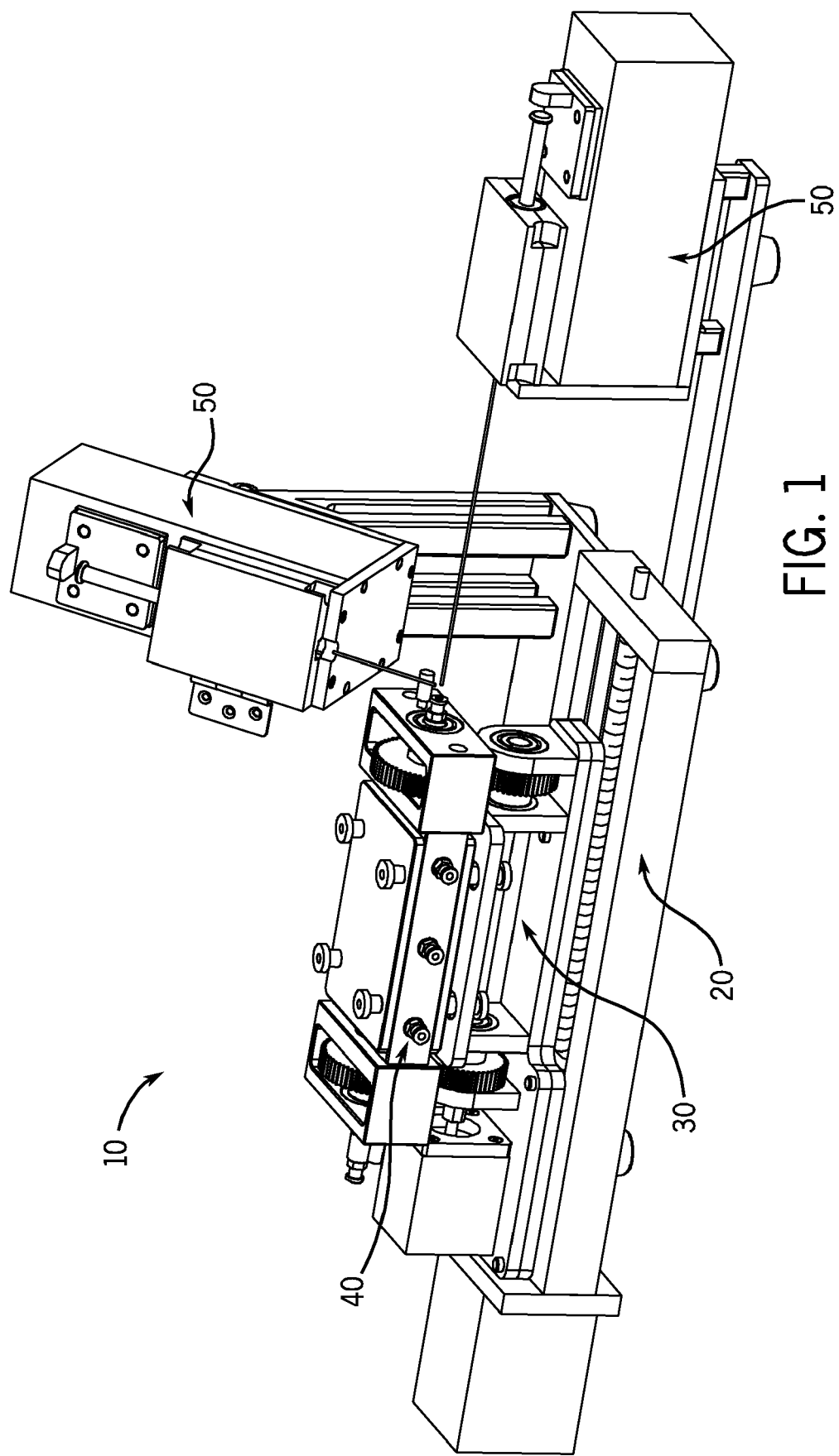
FIG. 1 is a perspective view of a cell seeding module in accordance with an embodiment of the invention.

The following description provides detail of various embodiments of the invention, one or more examples of which are set forth below. Each of these embodiments are provided by way of explanation of the invention, and not intended to be a limitation of the invention. Further, those skilled in the art will appreciate that various modifications and variations may be made in the present invention without departing from the scope or spirit of the invention. By way of example, those skilled in the art will recognize that features illustrated or described as part of one embodiment, may be used in another embodiment to yield a still further embodiment. Thus, it is intended that the present invention also cover such modifications and variations that come within the scope of the appended claims and their equivalents.

The cell seeding and growing apparatus of the present invention include a chamber having one or more grips rotatable along a longitudinal axis of the chamber and grips. The grips may be contained within the chamber and rotated independently or in unison within the chamber without rotating the chamber itself. Also included are one or more delivery systems, each delivery system including a delivery conduit having a portion aligned within the chamber. Further included are one or more linear actuators that linearly displace the grips relative to the delivery conduits and one or more rotary actuators that rotate the grips within said chamber relative to the delivery conduits. The linear actuator system may interlock with the chamber and, additionally, may interlock with the rotary actuator.

Alternatively, the cell seeding and growing apparatus may include one or more grips (independent and without being enclosed in a chamber system). The grips may be rotated independently or in unison about an approximately longitudinal axis. Also included is a delivery systems that has an approximately longitudinal axis and includes one or more delivery conduits aligned in linear relation with the longitudinal axis of the grips. The delivery conduits may further be aligned between grips. An actuator system may be included that interlinks the grips and rotates the grips either independently or in unison along a longitudinal axis of the grips. Another actuator system may be included to increase or decrease a distance between the grips and the delivery system. As the distance is increased or decreased, at least one of the grips and delivery system are displaced along a longitudinal axis of the same. Further the actuator systems may interlock and may be interchanged with other systems.

Alternatively, the system for seeding cells on a sample may include a chamber including at least two opposing grips for holding a sample, a rotary system coupled to the opposing grips (to rotate the grips about a longitudinal axis of the grips), one or more delivery systems (to deliver a media between the grips), and a linear actuator that linearly displaces at least one of the opposing grips and the delivery systems to thereby increase or decrease a distance between the grips and the delivery systems. The delivery systems may include a delivery conduit having at least a portion of the delivery conduit positioned within the chamber between the grips. The chamber may include one or more ports suitable for receiving at least one of a fluid delivery, a gas delivery, a temperature transducer, a flow transducer, a pressure transducer, or a linear displacement transducer. Further, the rotary system may interlock with the chamber and may also interlock with the linear actuator.

A user of the apparatus may use the apparatus to deliver or otherwise deposit media to a localized site on the sample. The media may include cells suspended in a solution, nutrients, fluids, gases or other substance. The sample may be secured to the grips in a manner suitable to rotate the sample around an axis of the sample, where the axis of the sample may be aligned approximately parallel with a surface of the sample to which the media is to be delivered. After selecting a sample and securing the sample to grips, the user may selectively rotate or linearly displace the sample along the sample axis. One or more delivery conduits may be used to deliver selected media to the sample. An embodiment of the invention includes aligning a first delivery end of a first delivery conduit of a delivery system with the sample. Additionally, a second delivery conduit, coupled to the same or separate delivery system, may be aligned with the sample. A site of the sample may be displaced relative to an end of the delivery conduit by rotating the sample, linearly displacing the sample along the axis of the sample or linearly displacing the conduit, while simultaneously or intermittently delivering media to the sample. Those skilled in the art will appreciate that it may be desired to deliver or deposit media on a tubular sample having a lumen extending through at least a portion of the sample. The user may align a second delivery conduit to either an exterior surface of the sample or to a surface within a lumen of the sample.

Turning attention now to the Figures, embodiments of the cell seeding module or system 10 of the present invention will now be described in more detail and are generally shown in FIGS. 1-3. Cell seeding module 10 includes a linear actuator system 20, a chamber grip actuator 30, an interchangeable chamber 40, cell delivery systems or modules 50, and controller 60. The cell delivery systems 50 are shown electrically coupled in parallel to controller 60 through electric leads 62-66. Although not shown, the linear actuator system 20 and chamber grip actuator 30 may also be electrically coupled to controller 60 or alternatively may be coupled to independent controllers.

Figure 4:
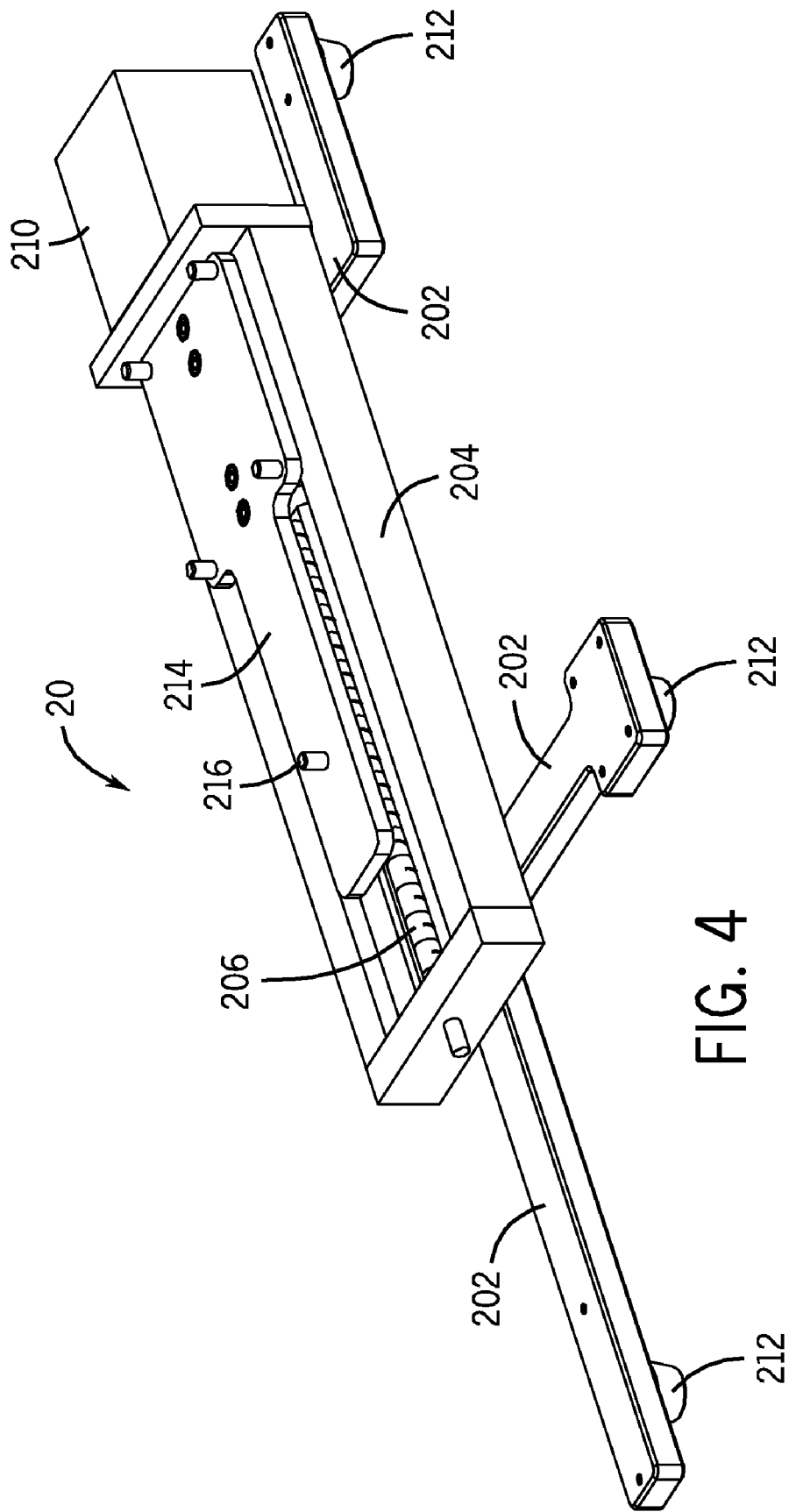
FIG. 4 is a perspective view of a linear actuator system suitable for use in the cell seeding module of the type shown in FIG. 1.
Figure 5:
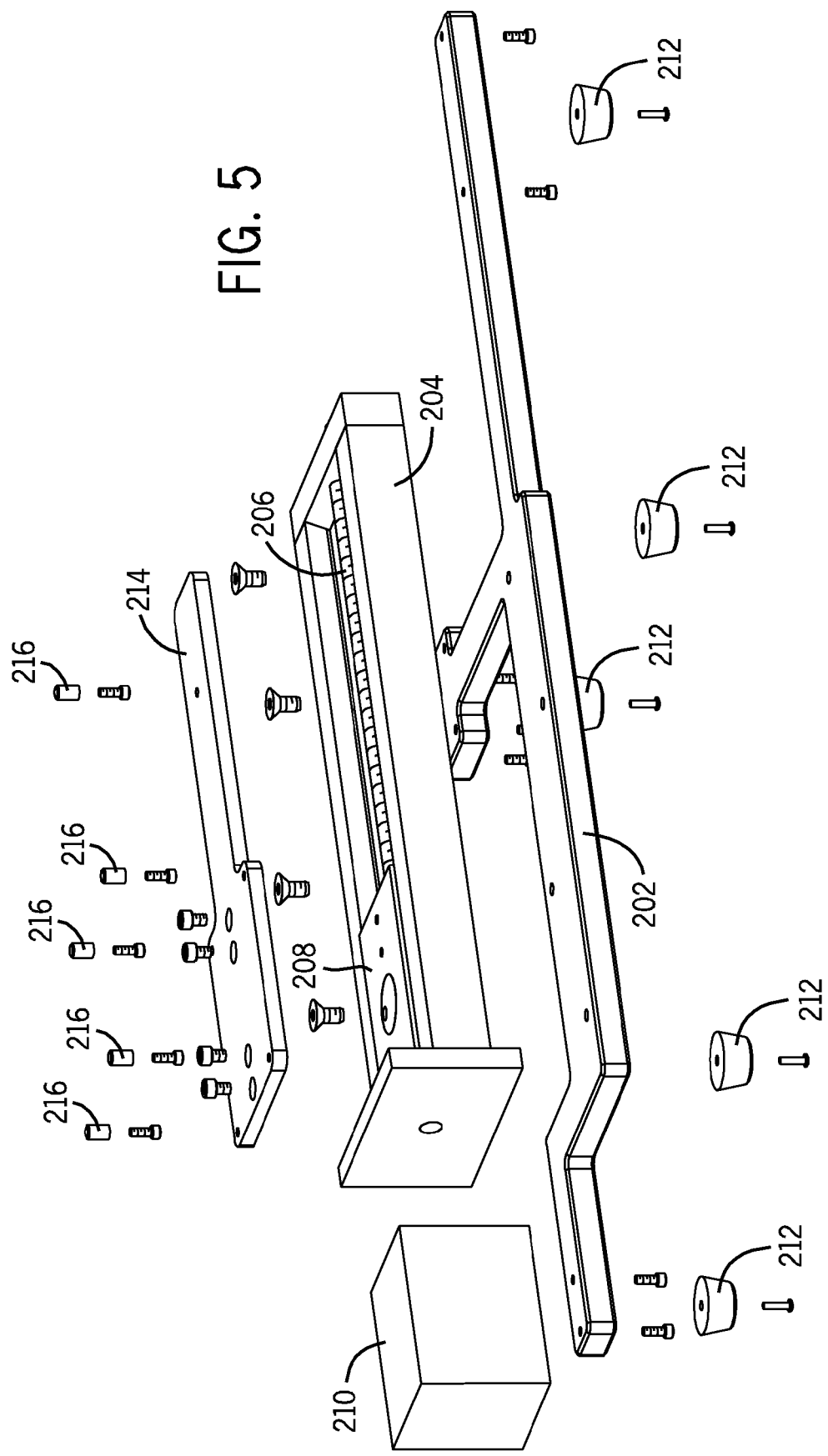
FIG. 5 is an exploded perspective view of a linear actuator system of the type shown in FIG. 4.

FIGS. 4 and 5 show generally an embodiment of the linear actuator system 20. Base plate 202 includes foot pads 212 attached to a bottom of the base plate 202. The foot pads 212 are slightly compressible so that when the cell seeding system 10 rests on an uneven surface, compression of the foot pads 212 compensate for the uneven surface and may be adjusted to keep the cell seeding system 10 level. Linear stage 204 is attached to base plate 202 and includes a worm 206 and worm gear base 208. Stepper motor 210 is coupled to worm 206. When stepper motor 210 is activated, the worm gear base 208 is actuated along worm 206 in either direction, depending upon the direction the worm 206 is turned by stepper motor 210. A mover base plate 214 is attached to the worm gear base 208, and includes guide pegs 216 attached to an upper surface of the mover base plate 214. The guide pegs 216 interlock with a mover top plate 302 of the chamber grip actuator system 30 (see also FIGS. 6 and 7). The interlocking of the linear actuator 20 and chamber grip actuator 30, provides for a quick interconnect and removal of the chamber system.

Figure 6:
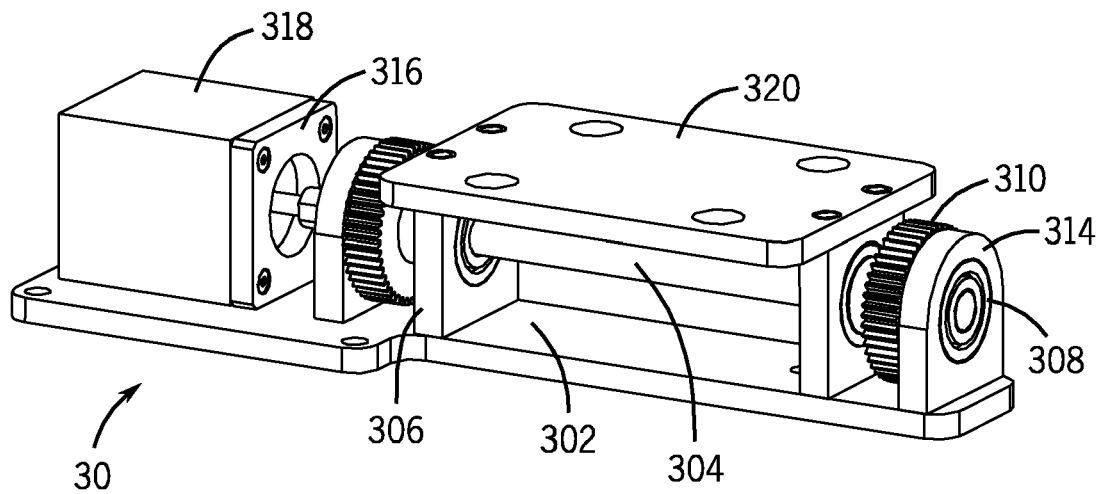
FIG. 6 is a perspective view of a chamber grip actuator suitable for use in the cell seeding module of the type shown in FIG. 1.
Figure 7:
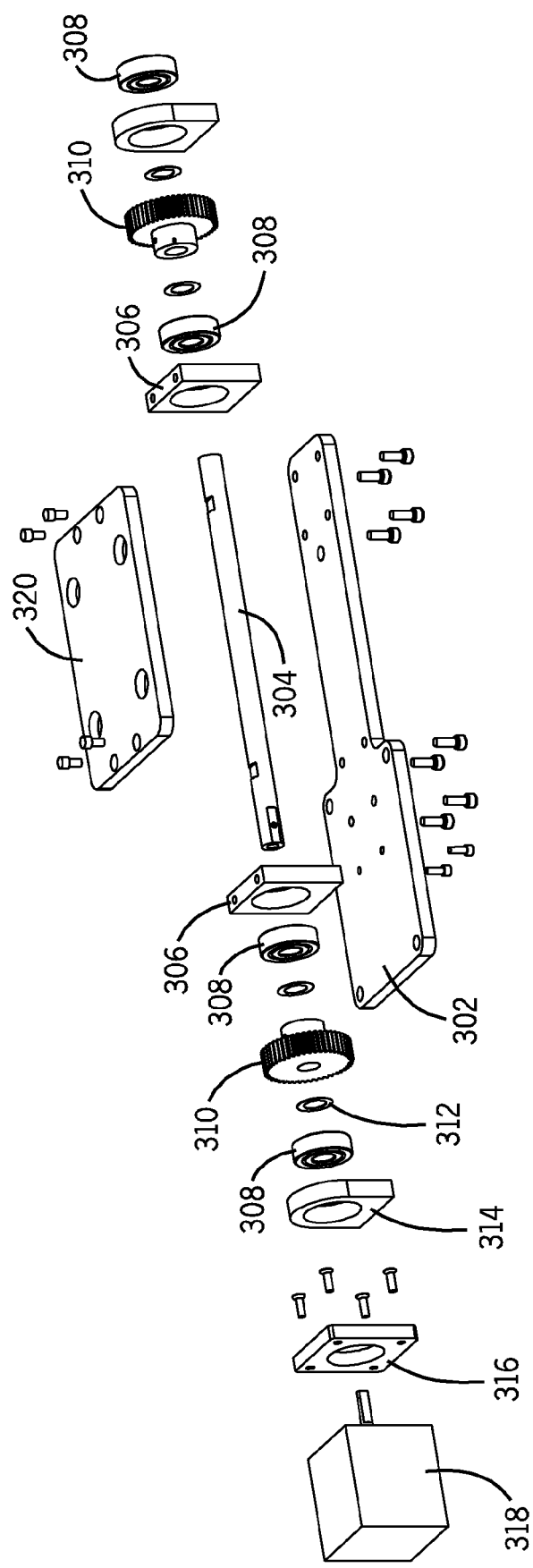
FIG. 7 is an exploded perspective view of a chamber grip actuator of the type shown in FIG. 6.

FIGS. 6 and 7 show an embodiment of the chamber grip actuator 30. Mover top plate 302 includes drive bar guide standoffs 306, drive bar guide 314 and motor plate 316 attached thereto. Drive bar 304 is positioned through apertures of the drive bar guide standoffs 306, drive bar guide 314 and motor plate 316 and an end of the drive bar 304 is coupled to rotary stepper motor 318. Drive gears 310 may be press fit or otherwise affixed to the drive bar 304. Bearings 308 are positioned within the apertures of drive bar guide standoffs 306 and drive bar guide 314. Drive bar guide 304 extends through bearings 308 which provides for a stable rotation of drive bar 304. Shims 312 are positioned between drive gear 310 and bearings 308 to ensure a space between drive gear 310, drive bar guide standoffs 306, and drive bar guide 314, and to reduce wear or rubbing of the drive gear 310 against the same. Chamber holder 320 is attached to a top portion of drive bar guide standoffs 306. Knurled nuts 430 are sized to fit within apertures extending through a top portion of chamber holder 320 and interlock or engage interchangeable chamber 40 with chamber grip actuator 30 (see also FIGS. 8 and 9). The interlock of the chamber grip actuator 30 and interchangeable chamber 40 provides for a quick interconnect of the chamber system. Activating rotary stepper motor 318 rotates drive bar 304 which consequently rotates drive gear 310.

Figure 8:
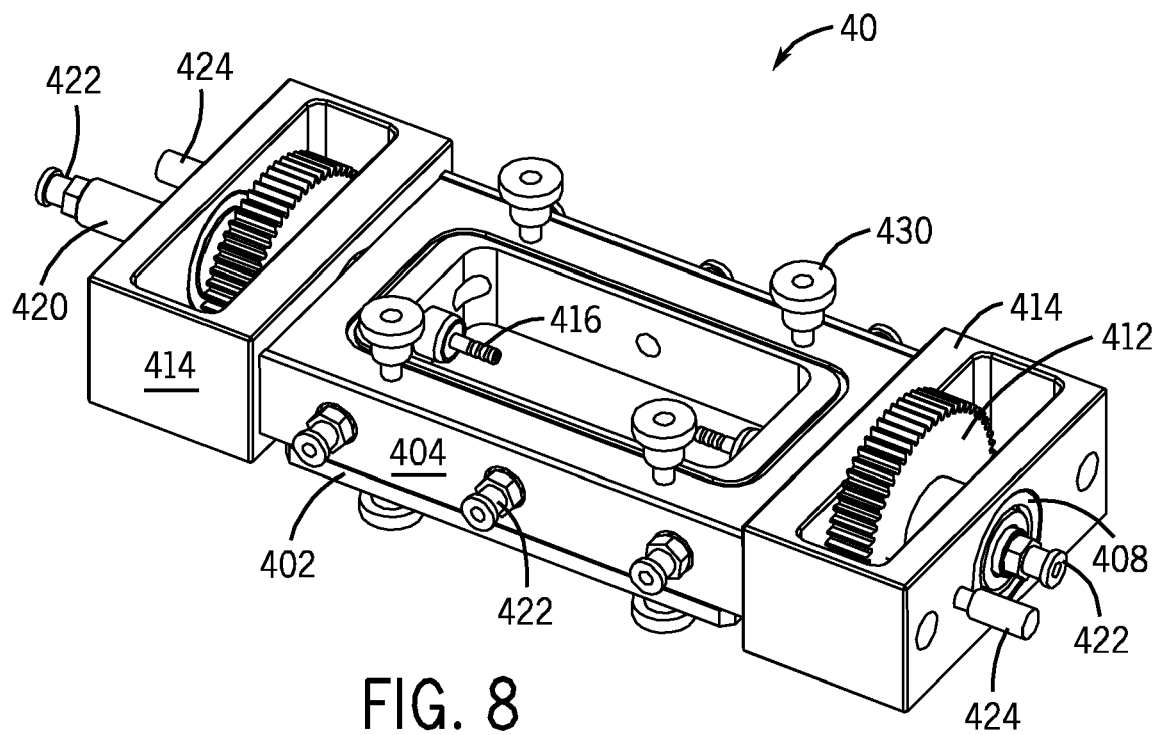
FIG. 8 is a perspective view of an interchangeable, portable, bioreactor chamber suitable for use with a chamber grip actuator of the type shown in FIG. 6.
Figure 9:
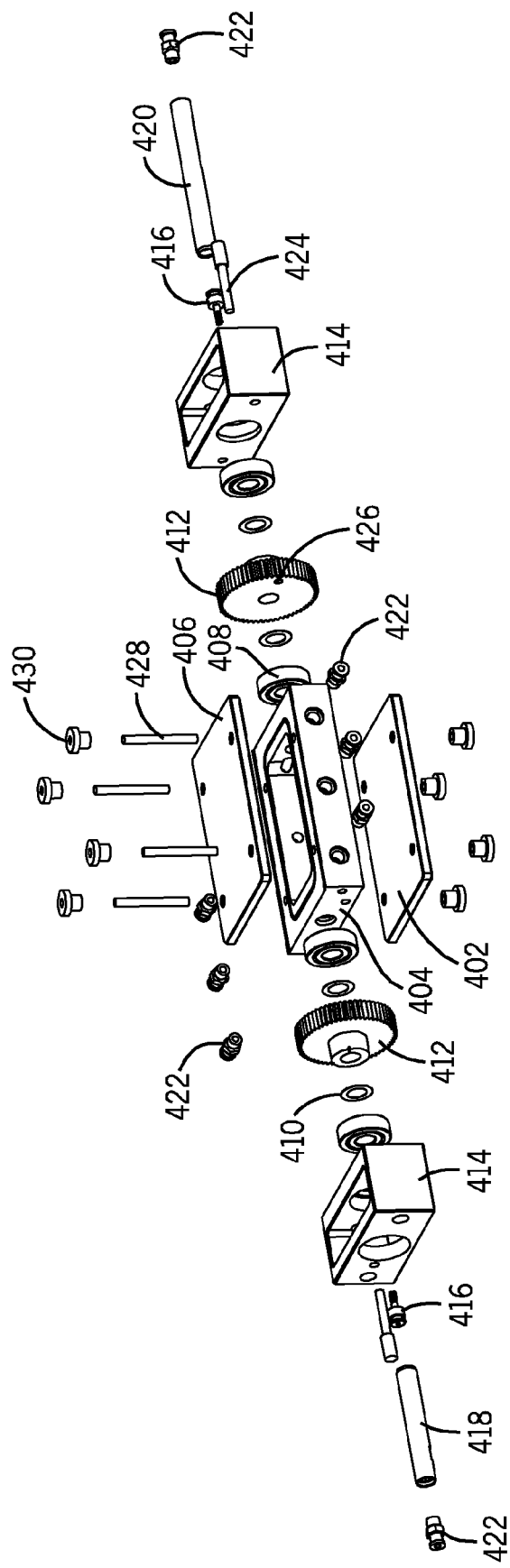
FIG. 9 is an exploded perspective view of a bioreactor chamber of the type shown in FIG. 8.

FIGS. 8 and 9 show an embodiment of the interchangeable, portable, autoclavable, bioreactor chamber 40. First sealing plate 402, chamber body 404, and second sealing plate 406 are held together by knurled nuts 430 and threaded rods 428 which extend through first sealing plate 402, chamber body 404, and second sealing plate 406. Knurled nuts 430 are positioned on each end of threaded rod 428 and may be turned to tighten the first sealing plate 402 and second sealing plate 406 against the chamber body 404. A seal may be positioned between the first sealing plate 402 and chamber body 404 and between the chamber body 404 and second sealing plate 406 to provide a seal between the respective same. The first and second sealing plates 402 and 406 may be of a suitable construction and one or both may be made of a transparent material.

A gear holder 414 is engaged to each end of the chamber body 404. Grip holder 418 is positioned through apertures of the gear holder 414 and chamber body 404. A follower gear 412 may be press fit or otherwise affixed to the grip holder 418. Bearings 408 are positioned within the apertures of gear holder 414. Grip holder 418 extends through bearings 408 which provides for a stable rotation of grip holder 418. Shims 410 are positioned between follower gear 412 and bearings 408 to ensure a space between follower gear 412, bearings 408 and gear holder 414 to reduce wear or rubbing of the follower gear 412 against the same. Likewise, grip holder 420 is positioned through apertures of another gear holder 414 and an opposite end of chamber body 404. A follower gear 412 may be press fit or otherwise affixed to the grip holder 420. Bearings 408 are positioned within the apertures of gear holder 414. Grip holder 420 extends through bearings 408 which provides for a stable rotation of grip holder 420. Shims 410 are positioned between follower gear 412 and bearings 408 to ensure a space between follower gear 412, bearings 408 and gear holder 414 to reduce wear or rubbing of the follower gear 412 against the same. Those skilled in the art will appreciate that the gear holders 414 may be attached instead to the chamber holder 320 and modified to interlock with chamber body 404.

Hollow grip holder 418 and 420 includes a grip 416 coupled to a first end of the respective grip holders 418 and 420 (first and second grips) and includes a Luer fitting 422 attached to an opposite end of each respective grip holder 418 and 420. Grip 416 may be a suitable construction adapted for holding a tissue, vascular grafts, biomedical prosthesis, medical devices or other desired specimen or sample. A tubular sample may slip over an end of the grip 416 and a relatively planar sample may, by way of example and without limitation, be sutured to an end of the grip 416. Also, grip 416 may include an aperture extending though a center axis of the grip to provide a passage between an interior lumen of the sample and the opposite end of the hollow grip holder 418 or 420. The grip ends of the grip holder 418 and 420 are positioned within an interior cavity of the chamber body 404 and may extend further or less within the cavity of chamber body 404 to accommodate samples of varying lengths. The grip holders 418 and 420 and grips 416 rotate within the cavity about a longitudinal axis of the chamber 30 or grip 416, without rotating the chamber 30 or chamber body 404.

Gear holder 414 further includes a gear lock pin 424 that may be actuated to engage within aperture 426 of follower gear 412. By engaging the lock pin 424 within the aperture 426 of follower gear 412, the grip holders may be restricted from rotating. Additional Luer fittings may be coupled to the chamber body and may be capped or may be utilized as ports suitable for receiving at least one of a fluid delivery, a gas delivery, a temperature transducer, a flow transducer, a pressure transducer, or linear displacement transducers. When first sealing plate 402 is engaged with chamber holder 320, drive gear 310 and follower gear 412 align and engage. Thus, when rotary stepper motor 318 rotates drive gear 310, follower gear 412 rotates which in turn rotates grip holders 418 and 420 and grips 416 in unison. Ultimately, the rotary or chamber actuation system rotates the sample coupled to grips 416 about a longitudinal axis of the chamber.

Figure 10:
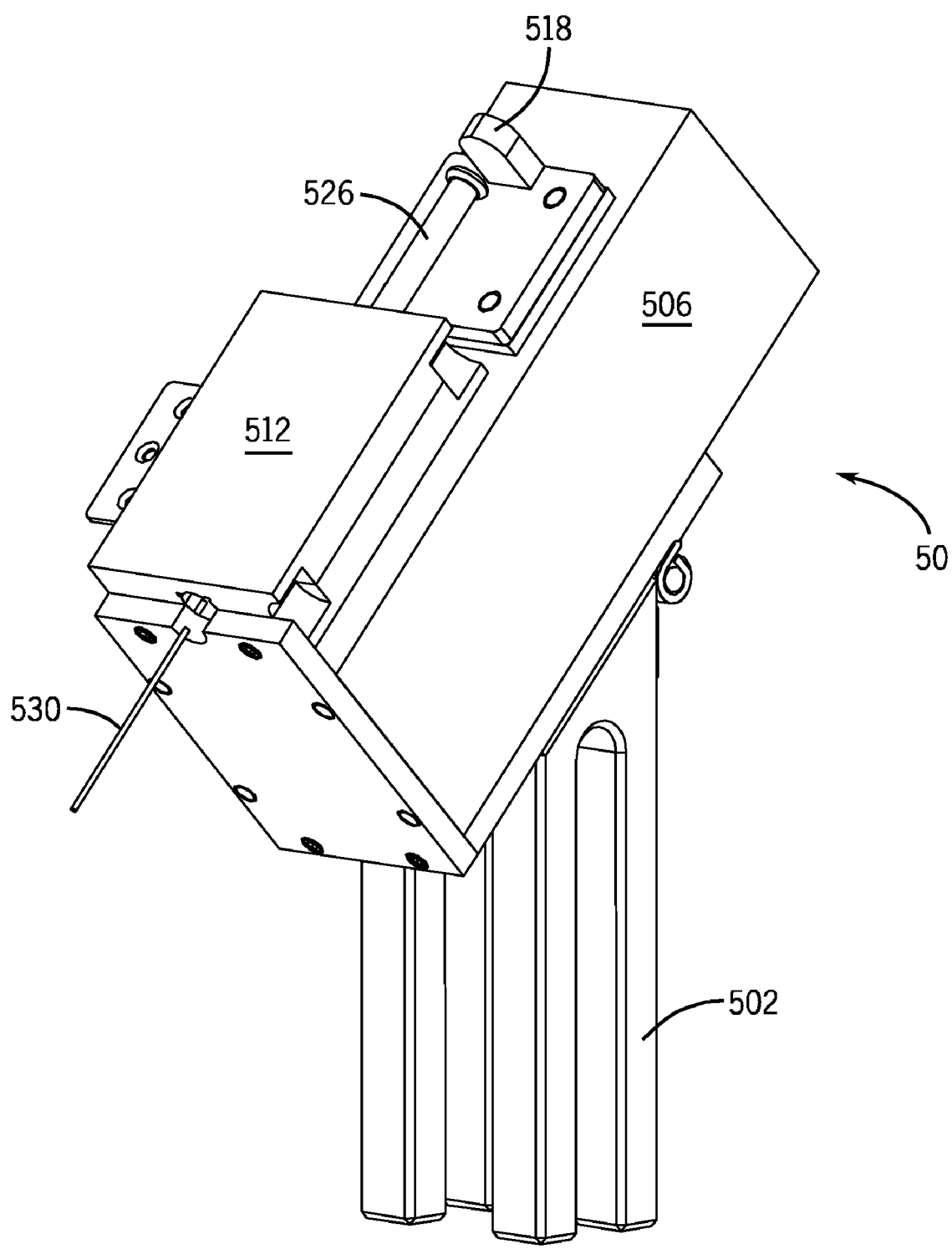
FIG. 10 is a perspective view of a delivery system suitable for use in the cell seeding module of the type shown in FIG. 1.

FIGS. 10 and 11 show an embodiment of the cell delivery module 50. A standoff 502 of each cell delivery module 50 is attached to the base plate 202 of the linear actuator 20 (shown in FIGS. 1 and 2). A base plate 504 is attached to the standoff 502 and stepper motor 506 or a manual linear stage (not shown) is attached thereto. A mover plate 522 is attached to stepper motor 506 via a worm drive (not shown) that linearly actuates the mover plate 522 back and forth in a longitudinal direction relative to the stepper motor 506. A syringe holder front plate 508 is attached to an end of the stepper motor 506. A syringe base plate 510 is fixed to the syringe holder front plate 508 and a syringe top plate 512 is attached to the base plate 510 with a hinge 516. A top plate catch 514 is positioned between the top plate 512 and base plate 510 to engage the top plate to the base plate. A top plate catch 514 may, for example without limitation, be a magnetic catch of known suitable construction. A push block plate 520 and syringe push block 518 are attached to mover plate 522. A syringe 524 of known suitable construction may be positioned between the top plate 512 and base plate 510, wherein a hollow needle or delivery conduit 530 and coupling 528 are attached in fluid communication to an end of the syringe 524. The hollow needle 530 may be made of a known suitable material, with a hollow stainless steel tube being preferred. The opposite end of syringe 524 includes a plunger 526 that draws fluid or gas into and pushes fluid or gas out of the opposite end of the syringe 524. Syringe push block 518 is actuated by stepper motor 506 and engages with an end of the plunger 526.

Having described the constructional features of embodiments of the invention, the mode of use will next be described. A user selects a desired sample or specimen and affixes the sample or specimen to the grip 416. For purposes of illustration and without limitation, a tubular sample will be described having each end attached to grips 416. A first delivery conduit 530 extends through Luer fitting 422, grip holder 420 and grip 416. An end of the delivery conduit 530 aligns within the chamber 30 and extends into the lumen of the sample. Those skilled in the art will appreciate that a nozzle may be attached to the end of the delivery conduit to control the flow and shape of the stream of fluid emitted from the end of the delivery conduit 530. A second delivery conduit may be aligned or positioned above and adjacent an exterior surface of the sample. Once the first and second delivery conduits are aligned in the desired position stepper motor 506 may be activated to push the syringe plunger 526, causing the contents of the syringe 524 to pass through the delivery conduit 530 and exit the open end of the delivery conduit 530. In this manner, cells suspended in drops of fluid, contained with the syringe 524, may be delivered to a selected and localized point on both the inner luminal surface of the sample and on an exterior of the sample.

Stepper motor 210 may be selectively activated to linearly displace grips 416 relative to delivery conduit 530 of delivery systems 50. Thus, this linear actuator or actuator system linearly displaces the grips relative to the delivery system along a longitudinal axis of the grip, chamber, and delivery system, thereby increasing or decreasing a distance between the grip and delivery system. Chamber grip actuator 30 and interchangeable chamber 40 together provide a rotary system or actuator system that rotates the grip 416 within the chamber around a longitudinal axis of the grip or chamber.

Stepper motor 210 may be activated in conjunction with activating stepper motor 506. In this manner drops of fluid are deposited on the exterior and interior of the sample in a straight line or row. Alternatively, rotary motor 318 may be activated in conjunction with activating stepper motor 506. In this manner drops of fluid are deposited on the exterior and interior of the sample to forms rings around the exterior and interior of the sample. In yet another embodiment both stepper motor 210 and rotary motor 318 may be activated in conjunction with activating stepper motor 506. In this manner, drops of fluid are deposited on the exterior and interior of the sample to create multiple variations of curvilinear patterns on the interior and exterior of the sample. Those skilled in the art will appreciate that altering the speeds of motors 210, 318, and 506, viscosity of the fluid, size of the cells, and size of the opening at the end of the delivery conduit 530 will all affect the amount of cells deposited at any given point on the sample. Further, motor 506 may be switched on an off while one or both of the other motors 210 and 318 remain activated to create row segments or curvilinear segments of cells on both the interior and exterior of the sample. Still further, the motors 506 on the first and second delivery systems may be switch on and off to vary the deposition of cells on the exterior of the sample in relation to the deposition of cells on the interior of the sample.

Those skilled in the art will further appreciate that different fluid suspended cells, fluid, pressurized air, gases or other media may be included in each delivery system syringe 524. For example, each delivery system may include a different cell type. Further, the size of the delivery conduit 530 may be selected to accommodate the size of the chosen specimen and cells to be delivered.

Although not required, cells can typically be contained within a cell composition or liquid carrier for the cells. The cell composition can be in the form of a suspension, solution, or any suitable form. Examples of suitable liquid carriers include, but are not limited to, water, ionic buffer solutions, and so forth. The use of a liquid carrier in the cell composition can ensure adequate hydration after depositing.

These and various other aspects and features of the invention are described with the intent to be illustrative, and not restrictive. This invention has been described herein with detail in order to comply with the patent statutes and to provide those skilled in the art with information needed to apply the novel principles and to construct and use such specialized components as are required. It is to be understood, however, that the invention can be carried out by specifically different constructions, and that various modifications, both as to the construction and operating procedures, can be accomplished without departing from the scope of the invention. Further, in the appended claims, the transitional terms comprising and including are used in the open ended sense in that elements in addition to those enumerated may also be present. Other examples will be apparent to those of skill in the art upon reviewing this document.

What is claimed is:

1. An apparatus for the deposit and growth of cells, comprising:
    a chamber including a first grip within said chamber, said first grip being rotatable about an approximately longitudinal axis of said chamber, without rotating said chamber;
    a first actuator system that rotates said first grip within said chamber;
    a first delivery system including a first delivery conduit, wherein at least a portion of the first delivery conduit aligns within said chamber;
    a second actuator system that linearly displaces said first grip relative to said first delivery conduit, wherein said first actuator is not aligned in series with said second actuator relative to the longitudinal axis of said chamber.

2. The apparatus as recited in claim 1, further comprising a second delivery system including a second delivery conduit, wherein at least a portion of said second delivery conduit aligns within said chamber, wherein said second actuator system also displaces said first grip relative to said second delivery conduit.

3. The apparatus as recited in claim 1, wherein said chamber further includes a plurality of ports suitable for receiving at least one of a fluid delivery, a gas delivery, a temperature transducer, a flow transducer, a pressure transducer, and a linear displacement transducer.

4. The apparatus as recited in claim 1, wherein said first actuator system interlocks with said chamber.

5. The apparatus as recited in claim 4, wherein said second actuator system interlocks with said first actuator system.

6. The apparatus as recited in claim 1, wherein said chamber further includes a second grip coupled to said first actuator system, wherein said first actuator system rotates said second grip about the approximately longitudinal axis of said chamber.

7. An apparatus for the deposit and growth of cells, comprising:
    a first grip rotatable about an approximately longitudinal axis;
    a delivery system having an approximately longitudinal axis;
    a first actuator system to rotate said first grip along said longitudinal axis of said first grip; and
    a second actuator system to increase or decrease a distance between said first grip and said delivery system, while displacing at least one of said first grip and said delivery system along a displacement axis, wherein said first actuator is not aligned in series with said second actuator relative to the longitudinal axis of said grip.

8. The apparatus as recited in claim 7, wherein said delivery system further comprises a first and second conduit aligned in linear relation with said longitudinal axis of said first grip.

9. The apparatus as recited in claim 7, further comprising a second grip coupled to said first actuator system, wherein said first actuator system rotates said second grip about an approximately longitudinal axis of said second grip.

10. The apparatus as recited in claim 9, wherein said first actuator system interlinks said first and second grip to thereby rotate said first and second grip in unison.

11. The apparatus as recited in claim 7, wherein said second actuator system interlocks with said first actuator system.

12. The apparatus as recited in claim 8, further comprising a second grip coupled to said first actuator system, wherein said first actuator system rotates said second grip about an approximately longitudinal axis of said second grip.

13. The apparatus as recited in claim 12, wherein said first and second conduits are aligned between said first and second grip.

14. An apparatus for seeding cells on a sample, comprising:
    a chamber including at least two opposing grips for holding a sample;
    a rotary system coupled to said opposing grips to rotate said grips about a longitudinal axis of said grips;

a first delivery system to deliver a media to a localized point between said grips; and a linear actuator that linearly displaces at least one of said opposing grips and said delivery system to thereby increase or decrease a distance between said grips and said delivery system, wherein said linear actuator and said rotary system are aligned in parallel relative to said longitudinal axis of said grips.

15. The apparatus as recited in claim 14, further comprising a second delivery system including a delivery conduit and having at least a portion of the delivery conduit positioned within said chamber between said grips.

16. The apparatus as recited in claim 15, wherein said linear actuator also displaces at least one of said opposing grips relative to said second delivery system.

17. The apparatus as recited in claim 14, wherein said chamber further includes a plurality of ports suitable for receiving at least one of a fluid delivery, a gas delivery, a temperature transducer, a flow transducer, a pressure transducer, and a linear displacement transducer.

18. The apparatus as recited in claim 14, wherein said rotary system interlocks with said chamber.

19. The apparatus as recited in claim 18, wherein said linear actuator interlocks with said rotary system.

\* \* \* \* \*